US009388930B2

(12) United States Patent
Servin

(10) Patent No.: US 9,388,930 B2
(45) Date of Patent: Jul. 12, 2016

(54) FLUIDIC INTERFACE VALVE ASSEMBLY WITH ELASTOMERIC FERRULE DEVICE

(71) Applicant: IDEX Health & Science LLC, Northbrook, IL (US)

(72) Inventor: Carl M. Servin, Rohnert Park, CA (US)

(73) Assignee: IDEX Health & Science LLC, Northbrook, IL (US)

( * ) Notice: Subject to any disclaimer, the term of this patent is extended or adjusted under 35 U.S.C. 154(b) by 248 days.

(21) Appl. No.: 14/025,415

(22) Filed: Sep. 12, 2013

(65) Prior Publication Data

US 2014/0102568 A1    Apr. 17, 2014

Related U.S. Application Data

(60) Provisional application No. 61/701,371, filed on Sep. 14, 2012.

(51) Int. Cl.
*F16L 47/00* (2006.01)
*F16K 3/08* (2006.01)
(Continued)

(52) U.S. Cl.
CPC ............... *F16L 47/00* (2013.01); *B01L 3/563* (2013.01); *F16K 3/085* (2013.01); *F16K 5/0278* (2013.01); *F16K 99/0013* (2013.01); *G01N 30/20* (2013.01); *B01L 2200/0689* (2013.01); *F16K 2099/0084* (2013.01); *F16K 2099/0086* (2013.01); *G01N 2030/202* (2013.01); *Y10T 137/9247* (2015.04)

(58) Field of Classification Search
CPC .... G01N 2030/202; G01N 30/20; F16K 3/08; F16K 3/085; F16K 5/0207; F16K 5/0257; F16K 5/0278; F16K 5/0292; F16K 5/04; F16K 5/0407; F16K 5/0457; F16K 5/0478; F16K 5/10; F16K 5/103; F16K 5/12; F16K 5/14; F16K 5/18; F16K 99/0013; F16K 2099/0084; F16K 2099/0086; F16K 47/00; B01L 3/563; B01L 2200/0689
USPC ............ 137/625.11, 625.12, 625.13, 625.18, 137/625.19, 625.31, 625.32, 625.46, 137/625.47; 251/309, 208, 209; 285/136.1, 285/136.11, 139.1–139.3, 141.1, 142.1, 285/205–208, 124.3, 124.4
See application file for complete search history.

(56) References Cited

U.S. PATENT DOCUMENTS 3,292,652 A * 12/1966 Gallone ................... H01J 9/38
137/246
4,243,071 A * 1/1981 Shackelford ........... G01N 30/20
137/625.46

(Continued)

*Primary Examiner* — William McCalister
*Assistant Examiner* — Ian Paquette
(74) *Attorney, Agent, or Firm* — Beyer Law Group LLP

(57) ABSTRACT

A tubing interface having an elongated tube, an elastomeric ferrule and a support ring device disposed around the ferrule. The ferrule includes a bore which is sized for receipt of the tube. The tubing interface further includes a cap member having an exterior surface, an opposed interior surface, and a tube receiving passage extending therethrough. The receiving passage is formed and dimensioned for axial sliding receipt of the tube member therethrough. The cap member further includes a cup-shaped receiving recess extending proximally from the interior surface, and is formed and dimensioned for axial receipt of the proximal end of the ferrule body member and the support ring. When the cap member is mounted to a valve apparatus, the support ring and the elastomeric ferrule device compressively cooperate with the cup-shaped recess to form a fluid-tight seal between the tube port and a communication port of the valve apparatus.

15 Claims, 15 Drawing Sheets

(51) Int. Cl.
  *F16K 99/00* (2006.01)
  *F16K 5/02* (2006.01)
  *B01L 3/00* (2006.01)
  *G01N 30/20* (2006.01)

(56) References Cited

U.S. PATENT DOCUMENTS

| | | | |
|---|---|---|---|
| 4,690,437 A | 9/1987 | Anderson, Jr. | |
| 4,969,938 A * | 11/1990 | America | G01N 30/6026 96/105 |
| 5,669,637 A | 9/1997 | Chitty et al. | |
| 6,273,478 B1 * | 8/2001 | Benett | F15C 5/00 285/338 |
| 6,319,476 B1 | 11/2001 | Victor, Jr. et al. | |
| 6,575,501 B1 * | 6/2003 | Loy, Jr. | F16L 19/0218 285/339 |
| 2002/0155033 A1 * | 10/2002 | Strand | B01J 19/0093 422/400 |
| 2009/0218813 A1 | 9/2009 | Helstern | |
| 2010/0000927 A1 * | 1/2010 | Beigel | B29C 43/18 210/198.2 |

* cited by examiner

FLUIDIC INTERFACE VALVE ASSEMBLY WITH ELASTOMERIC FERRULE DEVICE

RELATED APPLICATIONS

This application claims priority under 35 U.S.C. §119(e) from U.S. Provisional Patent Application No. 61/701,371, filed Sep. 14, 2012, entitled "SLOTTED FLUIDIC INTERFACE VALVE" which is incorporated by reference in its entirety.

FIELD OF INVENTION

The present invention relates generally to valve assemblies, and more particularly relates to multi-position valve assemblies in the field of DNA Sequencing, Invitro Diagnostics (IVD) and Analytical instruments. Additionally, the present invention relates to fluid connectors used for interfacing tubing to microfluidic devices.

BACKGROUND OF THE INVENTION

Rotary shear valve assemblies are often used in HPLC Analytical, Invitro Diagnostics (IVD) and DNA Sequencing machines. These valve assemblies are characterized by relatively long life and high precision fluid delivery. Many rotary valve assemblies are driven by stepper motors which are used for positioning a grooved rotor device to multiple locations on a stator device. Rotor and stator face seal components are manufactured of chemically resistant plastic materials such as PEEK, PFA, MFA, and UHMWPE. Additionally, chemical inertness may be achieved through use of ceramic rotor and stator face seal materials such as alumina and zirconia with the added benefit of exceptional long life and low wear.

Shear valve assemblies, traditionally manufactured using expensive machining methods, can be produced by means of low cost injection molding or die casting. Such parts include sun, planet and ring gears and housings containing these components.

One of the most expensive components to manufacture is the threaded stator. The stator consists of many features including ¼-28 UNF and 6-40 UNF threads for tubing connections, ferrule interfaces, and flat surfaces subjected to compression loads to seal against mating parts, all of which significantly increase part cost. Close tolerance features such as flatness and surface roughness are achieved by secondary operations such as polishing and machine lapping as well hand lapping. Other critical features include ports and through holes. Port dimensions are held to tight tolerances and surface finish in order to effectively seal under pressure when tubing is installed. Through holes are generally specified in sizes ranging from as large as 0.060 inches in diameter to as small as 0.006 inches. Also, it is desirable for valve designs to minimize the bolt circle of through holes in order to minimize contact sealing area and maximize system pressure. Smaller bolt circles are obtained by specifying angled rather than straight through holes. Often not only are holes machined at one angle but many are machined at compound angles. While most stators consist of 5 ports to 11 ports, some are now in production with as many 25 ports and 25 through holes. Rising stator cost can also be attributed to requirements for advanced high performance polymers such as PEEK and FEP to produce superior chemical resistance. Easily one can understand why the stator is among the most expensive valve components given its complexity and composition.

Multiple processes and techniques besides threaded stators are available to achieve fluidic connections. In the field of micro-fluidic chip design a common issue relates to the fluidic interface. Many struggle finding an efficient method of physically connecting the micro size fluidic transport channels on the chip to the macro-fluidic inlet and outlets for sample delivery and fluid output. Among the techniques being used is acrylic solvent bonding between a PMMA chip and PMMA union. Manually intensive techniques such as bonding usually result in inefficient time consumption and increased cost which are not appropriate for large scale production. Another technique is press fitting a needle into PDMS material which requires maintaining sufficient compression. However, the needle can damage the PDMS material causing undesirable leakage. Another option requires an adhesive ring bonded to PDMS. However, some users report poor adhesion to untreated PDMS and working pressures of 30 to 50 psi. Moreover, because of the adhesive ring, the product is a single use connection and not reusable. Alternatively, magnetic coupling is a unique, clean and inexpensive method incorporating a rubber cup which is compression sealed between two magnets and also seals around tubing. Many other variations of bonding, needle insertion and coupling have been tried and tested but none have achieved widespread success.

Most if not all fittings in the field of DNA Sequencing, Invitro Diagnostics (IVD) and Analytical instruments use an externally threaded member and single ferrule or ferrule assembly to create a fluidic seal. Such components are required to engage into an internally threaded part with a bore for holding the ferrule.

Accordingly, it is desirable to produce a cost effective valve assembly that can interface to fluidic connections without the use of a traditional stator and eliminate threading or troublesome bonding. While this invention may find use as a fluidic connection for micro-fluidic chip applications, its primary target is designs in which fluidic channels in a rotor direct liquid to multiple positions through a disk seal where a compressive force is applied to seal a disk surface against the rotor channel. The method of producing a sealed connection between the macrofluidic environment and the microfluidic disk seal while simultaneously applying a compressive sealing pressure between the disk seal and rotor is explained in the following sections.

SUMMARY OF THE INVENTION

The present invention provides a tubing interface assembly for a micro-fluidic valve apparatus which includes a disk surface and at least one fluid communication port terminating at the disk surface. The interface assembly comprises a tube apparatus including an elongated tube member, having a tube port at a distal end thereof, and an elastomeric ferrule device. The ferrule device includes a body member having a proximal end, a distal end, and a bore extending therethrough. The bore is formed and dimensioned for press-fit sliding receipt of the distal end of the tube member therethrough. The interface assembly further includes a cap member having an exterior surface, an opposed interior surface, and a tube receiving passage extending from the exterior surface to the interior surface thereof. The tube receiving passage is formed and dimensioned for axial sliding receipt of a transverse cross sectional dimension of the tube member therethrough. The cap member further defines a cup-shaped receiving recess extending from the interior surface toward the exterior surface. The cup-shaped receiving recess is formed and dimensioned for axial receipt of at least the proximal end of the ferrule body member such that at least a distal portion of the body member extends distally past the interior surface of the cap member. When the cap member is mounted to the valve apparatus in a manner aligning the tube port with the fluid communication port of the disk surface, the elastomeric ferrule device compressively cooperates with the cap member to form a fluid-tight seal between the tube port and the fluid communication port.

In one specific embodiment, the cap member defines a petal-shaped slot extending from the exterior surface to the interior surface thereof. The petal-shaped slot includes a ferrule passage portion on one side and tapers down to the tube receiving passage on an opposite end thereof. The ferrule passage is formed and dimensioned for sliding axial receipt of the ferrule device therethrough.

A significant advantage of this slotted cap and elastomeric ferrule aspects of this invention is that no threaded features are required for the fluidic sealing interface. In other words, neither an external thread on the ferrule fitting going into the slotted cap nor an internal thread in the slotted cap itself is required. The lack of such threaded features reduces production costs. Moreover, fluidic continuity is more simply achieved between the tube port of the tube member and the communication port of the stator disk surface by way of aligning the ferrule interface tubing assembly in the cupped seat recess of the slotted cap.

In another specific embodiment, the tube apparatus further includes a rigid support ring device disposed around a portion of the ferrule body member in a press-fit manner.

In still another configuration, the cup-shaped receiving recess is partially defined by a distally facing contact shoulder. This shoulder is formed to compressively seat and contact at least one of the ferrule body member and the support ring thereagainst.

Yet another embodiment, the ferrule body member includes a compression portion having a first diameter, and a crimp portion having a second diameter. The second diameter of the crimp portion is less than the first diameter of the compression portion where a ring contact shoulder is formed therebetween. The crimp portion is formed for sliding receipt of the support ring such that a distal edge thereof abuts against the ring contact shoulder for compressive deformation of the ferrule compression portion when the cap member is mounted to the valve apparatus.

In another aspect of the present invention, a tubing interface assembly is provided for a micro-fluidic valve apparatus wherein a disk surface thereof defines a plurality of fluid communication ports radially spaced about an axis thereof. The tubing interface assembly includes: a plurality of tubing assemblies and a rigid cap member. Each tubing assembly includes an elongated tube member having a tube port at a distal end thereof, an elastomeric ferrule device and a rigid support ring. The ferrule device includes a body member with a proximal end, a distal end, and a bore extending therethrough. Each bore is formed and dimensioned for sliding receipt of the distal end of the tube member therethrough. The rigid support ring is disposed around a portion of the respective ferrule body member. The interface assembly further includes a rigid cap member having an exterior surface, an opposed interior surface, and a plurality of tube receiving passage extending from the exterior surface to the interior surface thereof. These receiving passages are spaced thereabout in a manner such that each tube receiving passage is aligned with a respective one of the plurality of fluid communication ports disposed on the disk surface. Further, each tube receiving passage is formed and dimensioned for axial sliding receipt of a respective tube member therethrough. The cap member further defines a plurality of ferrule receiving recesses each corresponding to a respective tube receiving passage, and each extending proximally from the interior surface toward the exterior surface thereof, although not all the way through. Each ferrule receiving recess is formed and dimensioned for axial receipt of at least the proximal end of the ferrule body member and the support ring. When the cap member is mounted to the valve apparatus, each respective support ring and each respective elastomeric ferrule device compressively cooperate with the cap member to form a fluid-tight seal between each respective tube port and each respective fluid communication port.

In still another aspect of the present invention, a micro-fluidic valve apparatus is provided having a housing that defines a proximal opening, and a fluid distribution unit disposed in the proximal opening. The fluid distribution unit includes a proximal contact surface that defines two or more fluid communication ports. The valve apparatus further comprises a tubing interface assembly that includes is two or more tubing assemblies. Each tube assembly incorporates an elongated tube member with a tube port at a distal end thereof, and an elastomeric ferrule device with a body member. A bore thereof extends from a proximal end to a distal end thereof, and the bore is formed and dimensioned for press-fit sliding receipt of the distal end of the respective tube member therethrough. A rigid support ring is provided for each device disposed around a portion of the respective ferrule body member. In accordance with this aspect of the present invention, the valve apparatus further includes a cap member having an exterior surface, an opposed interior surface, and two or more tube receiving passages each extending from the exterior surface to the interior surface thereof. The tube receiving passage is formed and dimensioned for axial sliding receipt of a transverse cross sectional dimension of a respective tube member therethrough. The cap member further defines two or more cup-shaped receiving recesses each extending from the interior surface toward the exterior surface, and each corresponding to a respective tube receiving passage. The cup-shaped receiving recess is formed and dimensioned for axial receipt of at least the respective proximal end of the ferrule body member and the support ring such that at least a respective distal portion of the body member extends distally past the interior surface of the cap member. When the cap member is mounted to the housing, the respective tube ports are aligned with the respective fluid communication port of the disk surface. Each respective support ring and each respective the elastomeric ferrule device compressively cooperate with the cap member to form a fluid-tight seal between the corresponding tube port and the corresponding fluid communication port.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawings, in which:

DETAILED DESCRIPTION OF THE INVENTION

Figure 1:
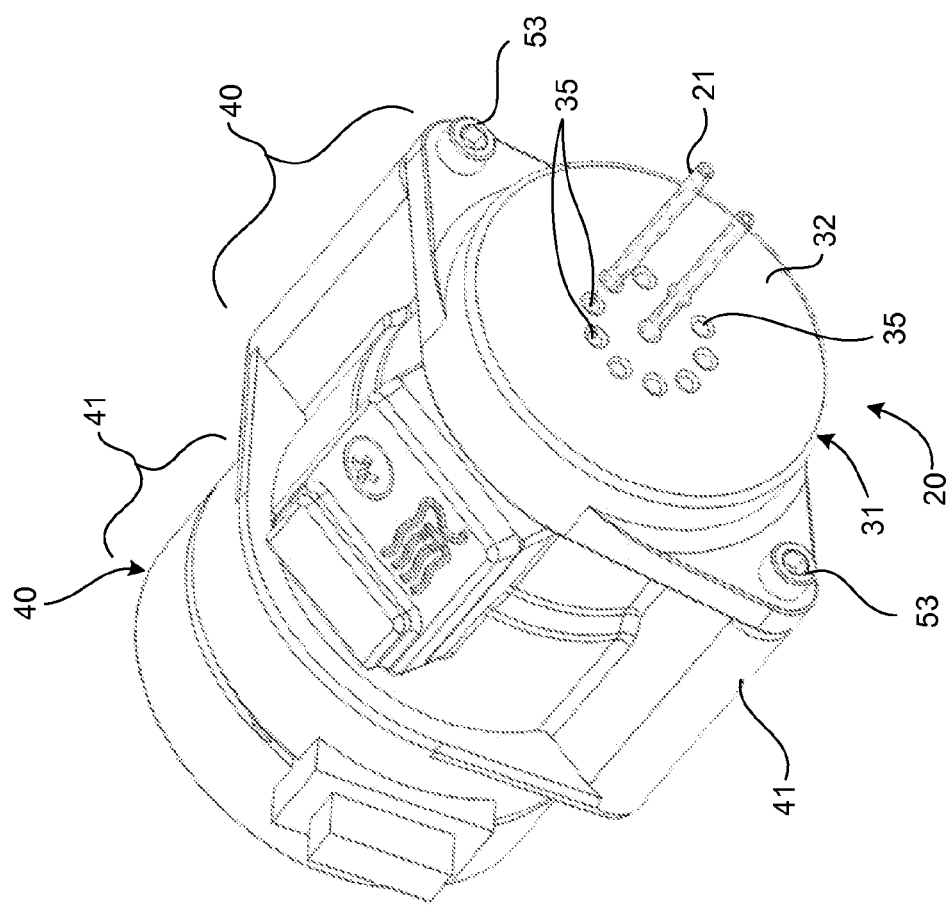
FIG. 1 is a top perspective view of a tubing interface assembly constructed in accordance with the present invention, and mounted to a micro-fluidic valve assembly.
Figure 2:
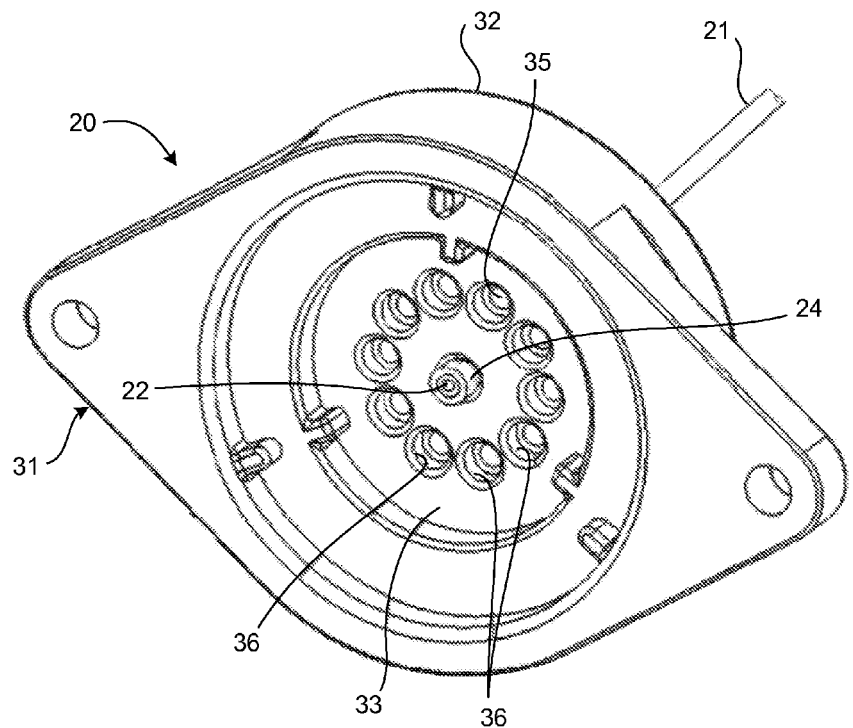
FIG. 2 is an enlarged bottom perspective view of the tubing interface assembly of FIG. 1.
Figure 3:
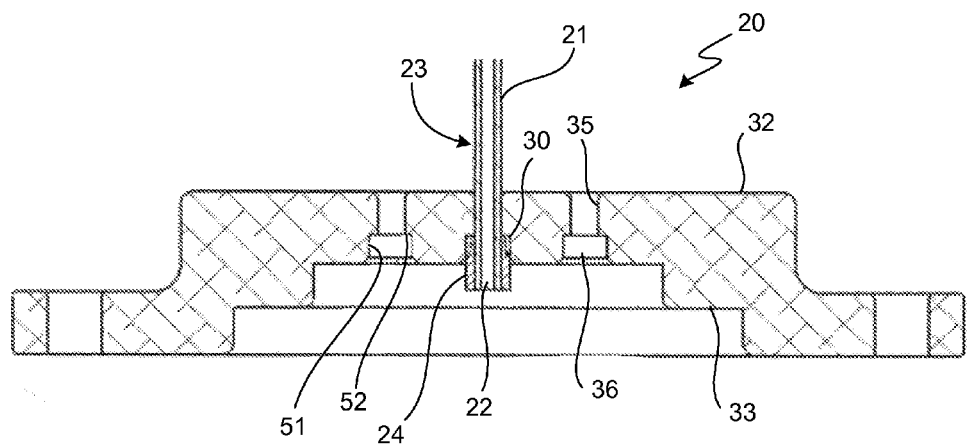
FIG. 3 is an enlarged side elevation view, in cross-section, of the tubing interface assembly of FIG. 1

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Referring now to FIGS. 1-4 and 13-15, a tubing interface assembly 20 is provided for a micro-fluidic valve apparatus 29 that enables relatively quick fluid-tight mounting thereto. The interface assembly 20 includes a tube apparatus 23 having an elongated tube member 21 which defines a tube port 22 disposed at a distal end thereof. An elastomeric ferrule device 24 is provided having a body member 25 with a proximal end 26, a distal end 27, and a bore 28 extending therethrough. The bore 28 is formed and dimensioned for press-fit sliding receipt of the distal end of the tube member 21 therethrough. In accordance with the present invention, the tube apparatus 23 includes a rigid support ring 30 disposed around a portion of the ferrule body member 25. A cap member 31 cooperates with the tube interface assembly 20 for fluid-tight mounting thereof to the micro-fluidic valve apparatus 29. The cap member 31 includes an exterior surface 32, an opposed interior surface 33, and a tube receiving passage 35 extending from the exterior surface to the interior surface thereof. The tube receiving passage 35 is formed and dimensioned for axial sliding receipt of a transverse cross-sectional dimension of the tube member therethrough. The cap member 31 further defines a cup-shaped receiving recess 36, in communication with the tube receiving passage, extending from the interior surface 33 toward the exterior surface 32. The cup-shaped receiving recess 36 is formed and dimensioned for axial receipt of at least the proximal end of the ferrule body member 25 and the support ring 30 such that at least a distal portion of the body member 25 extends distally past the interior surface 33 of the cap member 31

Figure 4:
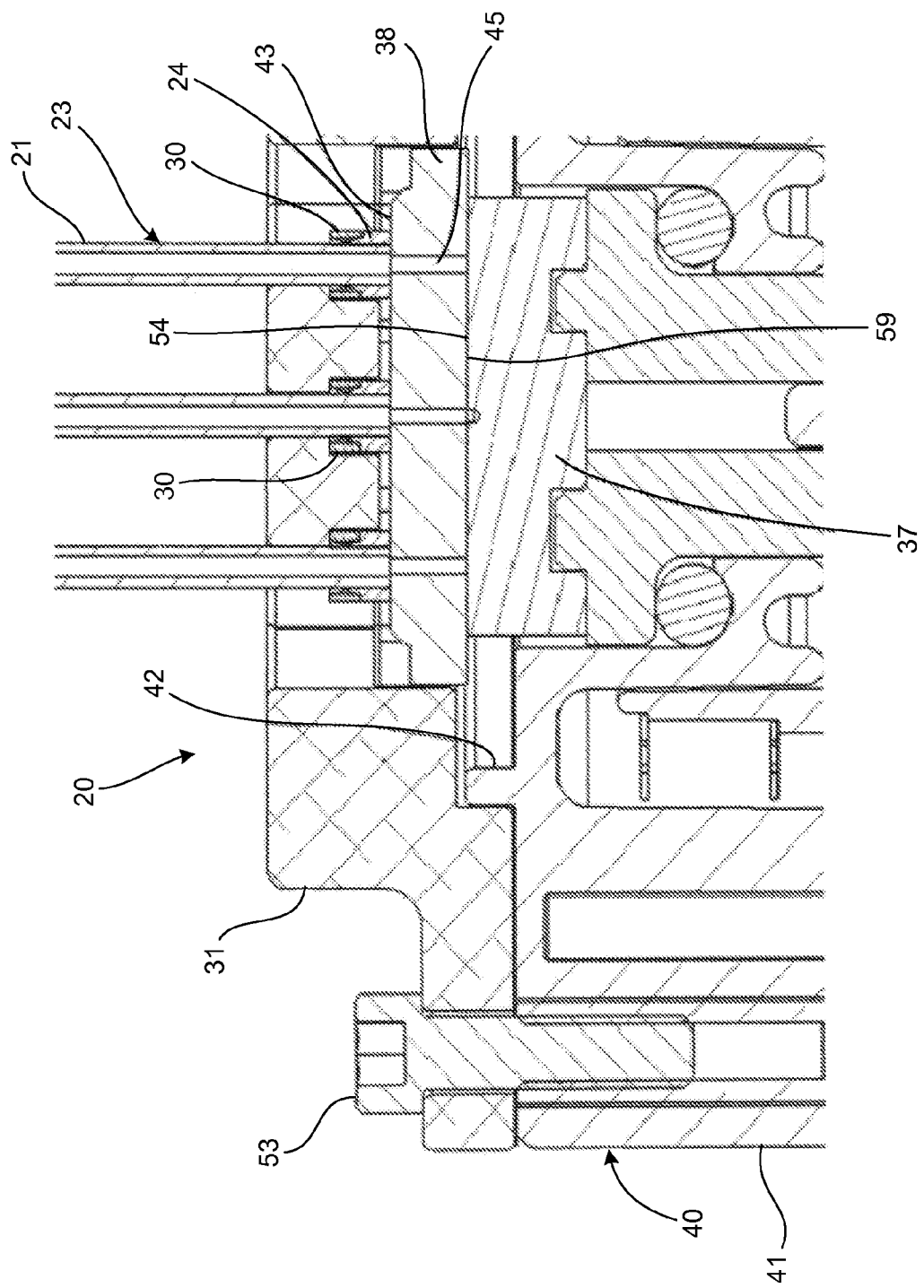
FIG. 4 is a fragmentary, enlarged, side elevation view, in cross-section, of the tubing interface assembly and the micro-fluidic valve assembly of FIG. 1.

Briefly, FIGS. 1 and 4 best illustrate that the micro-fluidic valve apparatus 29, in one specific embodiment, is a rotor-type valve incorporating a rotor device 37 and a stator device 38 upon which the tubing interface assembly 20 is fluidly coupled to. The rotor device 37 and the stator device 38 are supported in an actuator assembly 40 which in turn is coupled to a rotor drive assembly 41. The actuator assembly 40 includes a housing 41 which defines an opening 42 upon which the stator device 38 is disposed. A relatively planar backside disk surface 43 of the stator device 38 is exposed in the housing opening 42 upon which the tubing interface assembly 20 cooperatively mounts. Hence, in accordance with the present invention, when the cap member 31 is mounted to the housing 41 of the actuator assembly, the tube port 22 of the tube apparatus 23 is fluidly aligned with a corresponding fluid communication port 45 defined in the proximal disk surface 43 of the stator device.

Simultaneously, the elastomeric ferrule device 24 is compressed between this proximal stator disk surface 43, on one side, and the rigid support ring 30 on the other side. In turn, each support ring 30 is further compressed against a corresponding cup-shaped recess, in accordance with the present invention, simultaneously forming a fluid-tight seal between the tube port 22 and the fluid communication port 45. Hence, corresponding multiple points are created to channel both inlet and outlet flow to the macro-fluidic environment.

Accordingly, a quick mount tubing interface assembly is provided for a micro-fluidic valve apparatus that eliminates the prior art fluidic sealing interfaces that require external threaded features on the ferrule fitting and/or internal threaded feature in the cap member itself. The absence of such threaded features not only reduce production costs, but achieve simple and simultaneous fluidic continuity between the respective tube port 22 of the respective tube apparatus 23 and the corresponding fluid communication port 45 on the stator disk surface 43.

Moreover, in the specific embodiments shown in FIGS. 6-11, to promote even quicker fluid coupling between the tubing interface assembly and the cap member 31, the cap member further defines one or more petal-shaped slots 46. Each slot corresponds to, and is in fluid communication with, a respective tube receiving passage 35 thereof. Moreover, the respective petal-shaped slots 46 each include a larger diameter ferrule passage portion 47, on one side, and taper down to the smaller diameter tube receiving passage 35 on an opposite end thereof (at least on the exterior surface side of the cap member).

Figure 8:
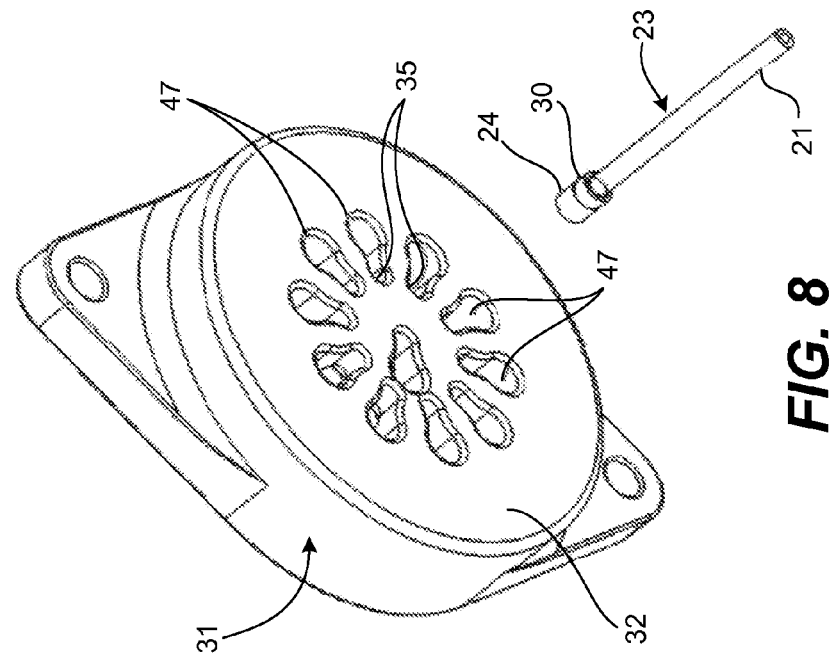
FIG. 8 is an enlarged, top perspective view of the slotted cap member of the alternative tubing interface assembly of FIG. 6, prior to insertion of a tube apparatus.
Figure 7:
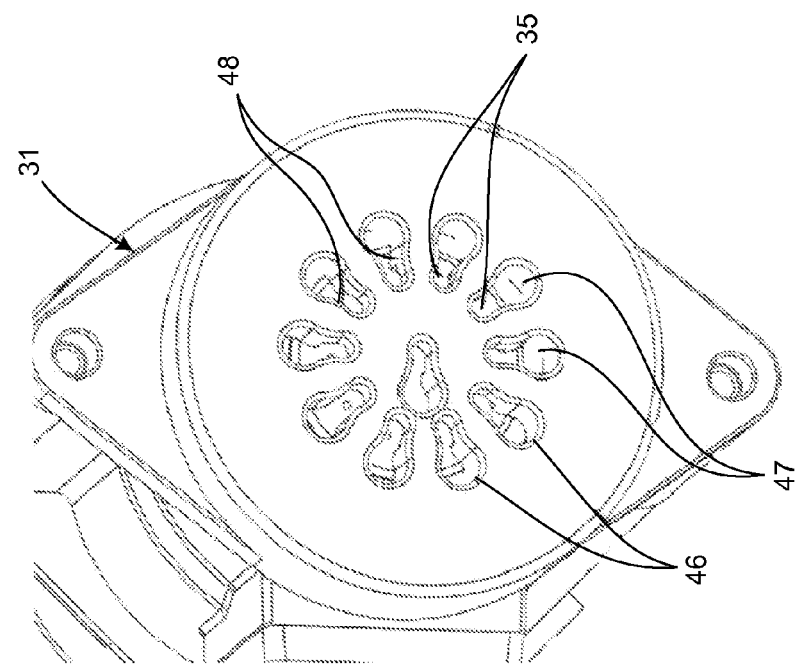
FIG. 7 is an enlarged, top perspective view of the alternative tubing interface assembly of FIG. 6.
Figure 9:
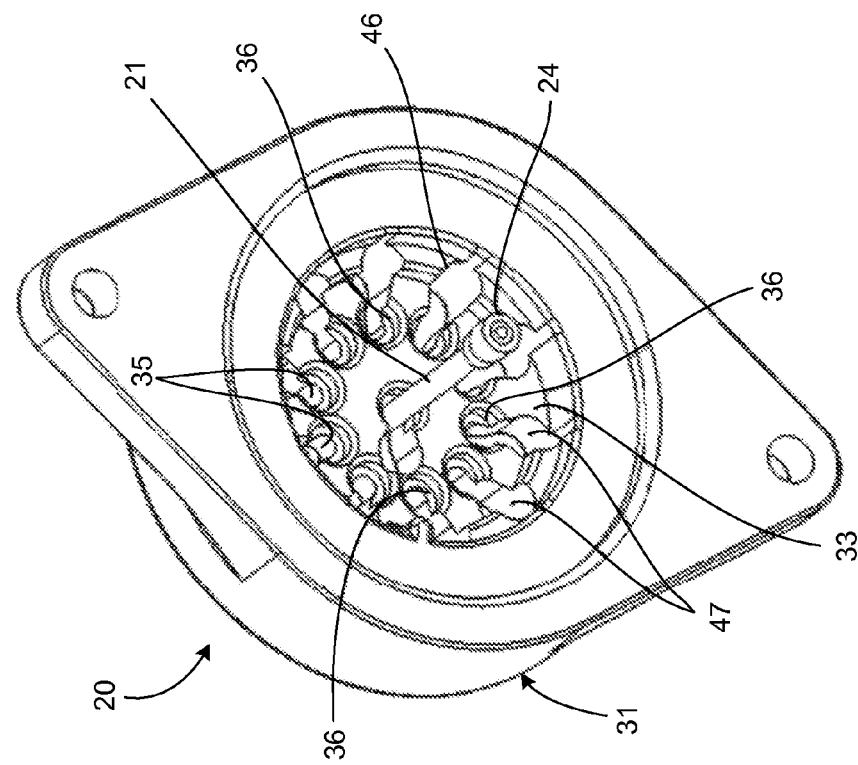
FIG. 9 is a bottom perspective view of the slotted cap member of FIG. 8 with the tube apparatus partially secured thereto.

As best illustrated in FIGS. 8 and 9, each elastomeric ferrule device 24 is to be initially axially aligned with, and subsequently passes or slides through the larger diameter ferrule passage portion 47 from the proximal disk surface 43 side of the cap member. The ferrule passage portion 47, thus, is sized and dimensioned to slideably receive the transverse cross-sectional dimension of the elastomeric ferrule device 24 therethrough. Once the elastomeric ferrule device 24 and the corresponding support ring 30 are positioned distally past the cap member interior surface 33, the respective tube member 21 is passed into the tapered channel 48 and slideably engages into the respective, smaller diameter tube receiving passage 35 (FIG. 9). Accordingly, the tube receiving passage 35 is sized and dimensioned to permit sliding or press-fit receipt of the tube member 21 therein, but not permit axial withdrawal or pullout of the elastomeric ferrule device 24 therethrough.

Figure 11:
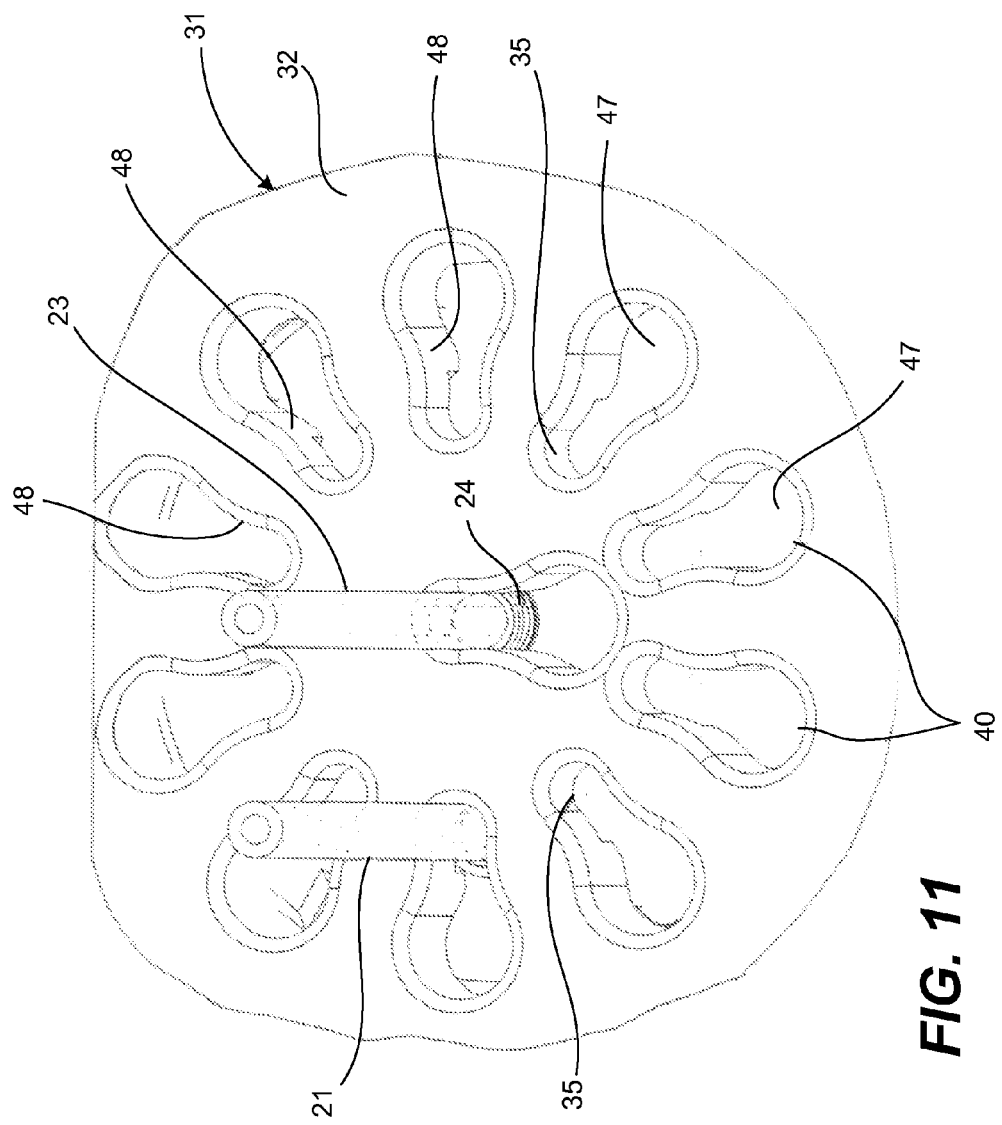
FIG. 11 is a fragmentary, enlarged, top perspective view of the slotted cap member of the tubing interface assembly of FIG. 6, showing mounting of the tube apparatus.

In one specific embodiment, the tube receiving passage 35 is more specifically sized and dimensioned to enable lateral friction fit, or press fit snap, receipt (FIGS. 9 and 11). Each tapered channel 48 and the tube receiving passage 35 of the petal-shaped slot 46, however, is sufficiently sized, dimensioned and toleranced to prevent passage of the larger diameter elastomeric ferrule (5) axially therethrough, thereby preventing the tubing interface assembly 20 from falling out.

Figure 10:
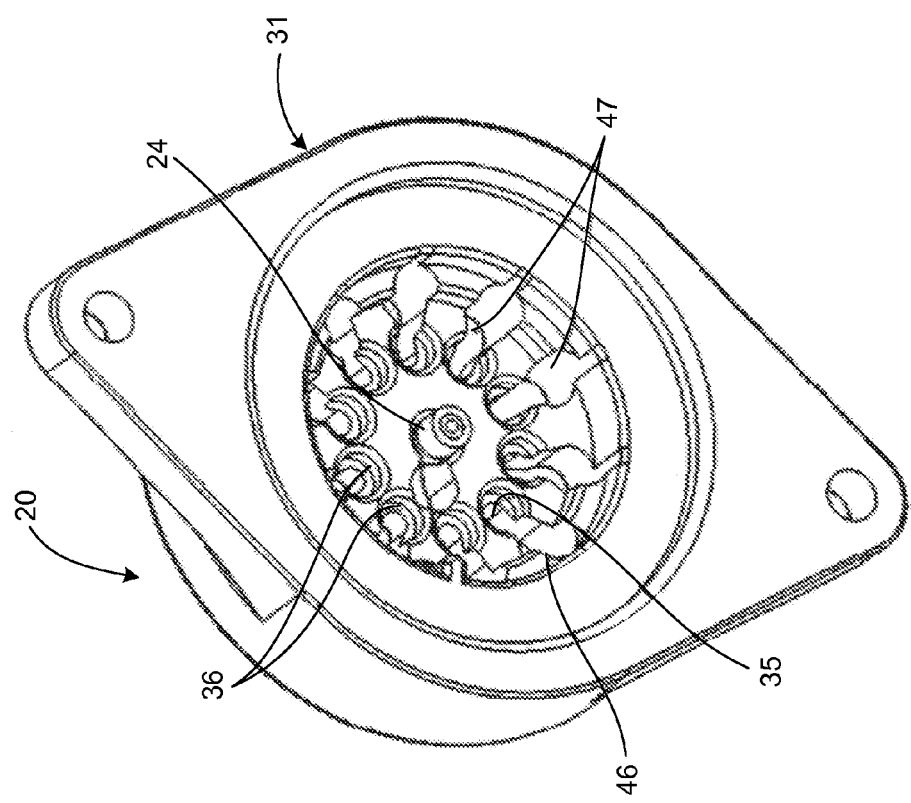
FIG. 10 is a bottom perspective view of the slotted cap member of FIG. 8 with the tube apparatus fully seated.
Figure 12:
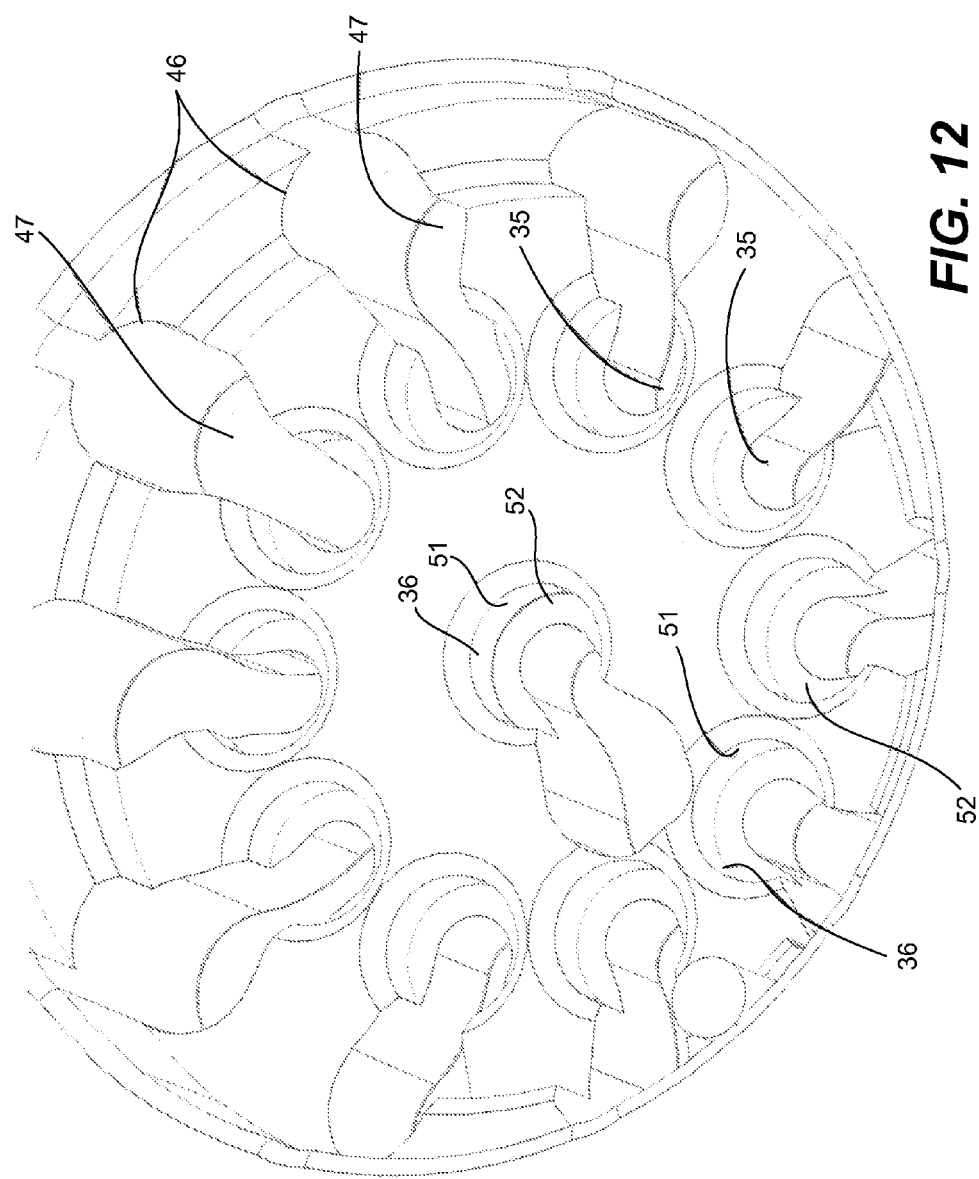
FIG. 12 is a fragmentary, enlarged, bottom perspective view of the slotted cap member of the tubing interface assembly of FIG. 6.

Referring now to FIGS. 9, 10 and 12, once the tube member 21 is press-fit or received in the tube receiving passage 35, a proximal portion 50 of the elastomeric ferrule device 24 and/or the corresponding support ring 30 can be proximally received in the cup-shaped receiving recess 36. This cupped seat 36, formed in the underside interior surface 33 of the cap member, is sufficiently sized to enable partial axial receipt of the rigid support ring 30, as well as the proximal portion 50 of the elastomeric ferrule device therein, while at the same time provide structural support under compressive forces.

The interior walls defining each cup-shaped receiving recess 36 preferably mirror that of the exterior surface of the proximal portion of the elastomeric ferrule device 24, albeit slightly larger. For instance, each receiving recess 36, as shown in FIG. 12, is defined by an interior cylindrical wall 51, and a distally facing compression shoulder 52. Accordingly, as the proximal portion of the elastomeric ferrule device 24 and the corresponding support ring 30 are axially withdrawn and seated in the receiving recess 36, axial support is provided as the ferrule proximal end abuts against the compression shoulder 52, while lateral support is provided by engagement between the side walls of the ferrule device and corresponding support ring with the cylindrical wall 51.

The partial receipt of the corresponding proximal portion 50 of the ferrule device 24 provides the dual function of seating, securing and aligning the ferrule device relative to the cap member, and further axially positioning the orientation of the distal end of the tube member 21, as well as that of the ferrule device 24. Hence, when the cap member 31 is secured to the housing 41 or valve actuator, via the corresponding aligned bolts 53, etc., each elastomeric ferrule device 24 is simultaneously fluid-tight sealed to and around the corresponding fluid communication port 45 of the disk surface 43.

One important benefit of these petal-shaped slots 46 is to allow the tube member 21 of the tubing interface assembly 20 to be easily removed and replaced. For example, on the opposite side of the ferrule side of the tubing, one may install a larger fitting (e.g. ¼-28) to connect to a macro-fluidic device (e.g. pump, reservoir, waste). Such a macro-fluidic fitting will most likely be too large to fit through the smaller diameter tube receiving passage 35 of the slotted cap member. However, the sizes of the elastomeric ferrule and petal features of the slotted cap are specifically designed to allow the elastomeric ferrule to engage into the petal feature and fit in the cupped seat of the slotted cap member. Hence, any size fitting of the customer's choice on one end of the tubing is allowed, using the proper adapters, while the other end contains the elastomeric ferrule device 24 described above.

Figure 14:
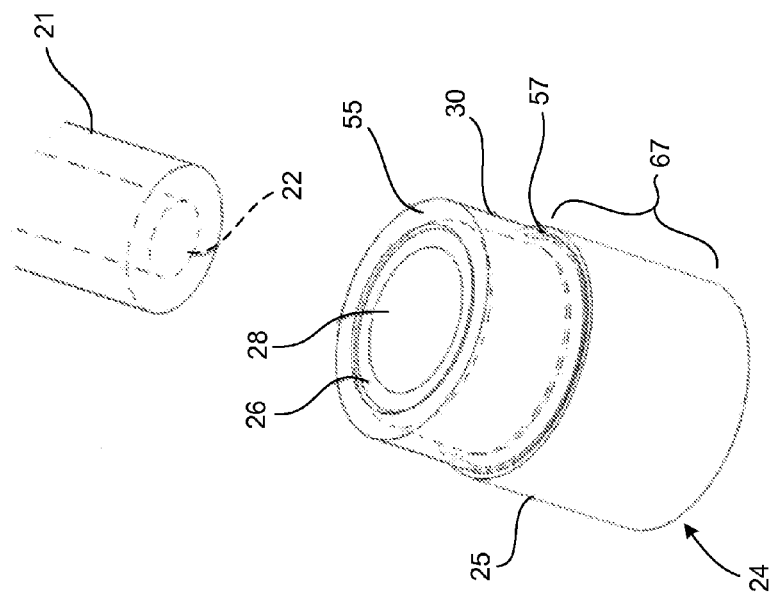
FIG. 14 is a partially exploded, top perspective view of the distal portion of the tube apparatus of FIG. 13.
Figure 13:
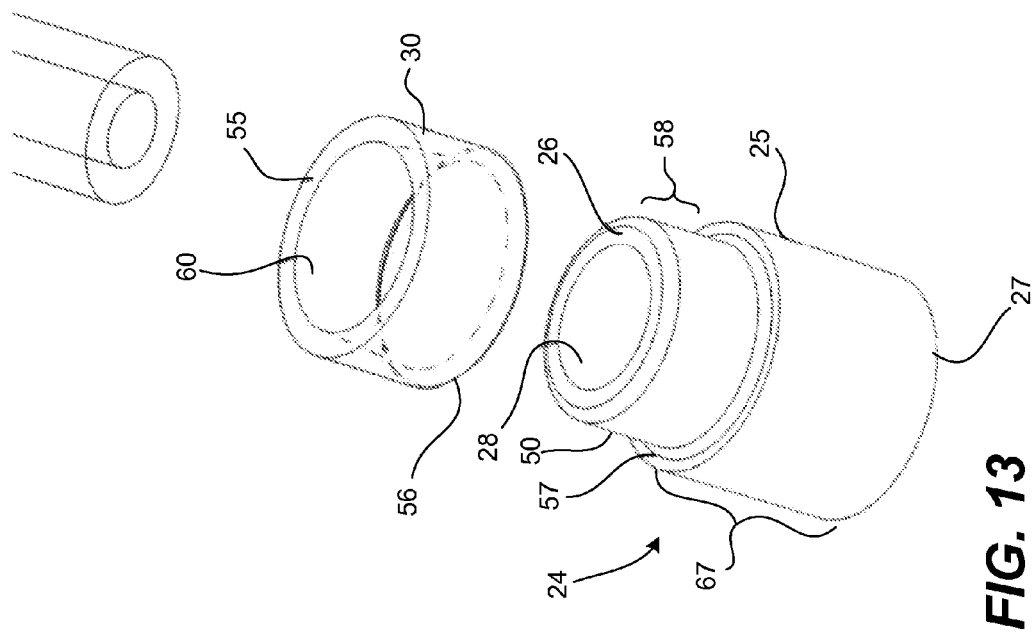
FIG. 13 is an enlarged, exploded, top perspective view of the distal portion of the tube apparatus of the present invention.
Figure 15:
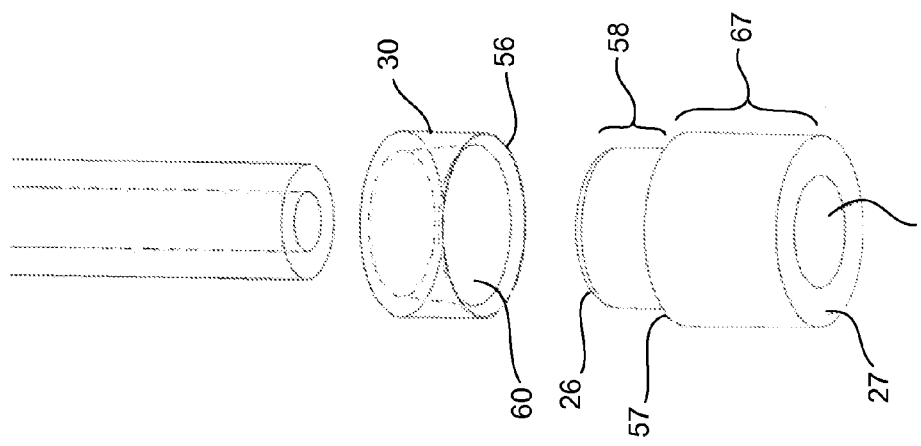
FIG. 15 is an exploded, bottom perspective view of the distal portion of the tube apparatus of FIG. 13.

As best shown in FIGS. 13-15 and as mentioned above, the tube apparatus 23 collectively includes the elastomeric ferrule device 24, rigid support ring 30 and the elongated tube member 21. By substituting a rigid ferrule device with an elastomeric ferrule device, three purposes are served. First, the elastomeric ferrule device 24 is sized and dimensioned for axial passage through the ferrule passage portion 47 of the petal-shaped slot 46, enabling simple insertion and removal therefrom. Secondly, the elastomeric ferrule device 24, together with the support ring 30 provides a fluid-tight pressure seal when the ferrule distal end 27 thereof is compressed against the proximal disk surface 43 of the stator device 38.

Lastly, the when the elastomeric ferrule device is compressed, an opposite a spring force is created by the body member 25 in its compressed state. The collective compression of the plurality of elastomeric ferrule devices during assembly and mounting of the slotted cap member to the housing 41 or actuator body, via bolts or screws 53, for example, generate the compression force necessary to create the fluid-tight seal. The elastomeric ferrule device, may be compressed in the range of about 10% to about 70% of its original height. Given an elastomeric material with elastic modulus in the range of about 500 psi to about 20,000 psi, such as santoprene, polyethylene, or fluoroelastomer compounds for instance, a single elastomeric ferrule device with a diameter in the range of about 0.100 inch to about 0.180 inch, and height in the range of about 0.02 inch to about 0.08 inch, can alone achieve a compression spring biasing force in the range from a few pounds to about 100 lbf.

As mentioned above, the valve actuator body consists primarily of the valve or actuator housing 41, the rotor device and the stator disk device each of which butt against one another. In many conventional applications, a compressive force in the range of at least about 30 lbf between the rotor face 54 and stator face 59, at the stator/rotor interface, is sufficient to create a fluid-tight seal when the rotor and stator device materials are either polymer or ceramic.

It will be appreciated that when multiple fluid connections are desired, a balanced distribution of elastomeric ferrule devices 23 is necessary to achieve a uniform application of compression pressure. Such a non-uniform pressure profile may result in skewed loading across the rotor/stator interface which results in leakage between the rotor face and stator face. Accordingly, the distribution of elastomeric ferrule devices 23 should be symmetrical oriented around the disk surface 43, and the about a rotational axis of the valve actuator assembly 40.

By way of example, referring back to FIGS. 4 and 6, the complete micro-fluidic valve apparatus 29 is illustrated with the plurality of tubing interface assemblies 20 (e.g., in FIG. 6 a total of eleven interface assemblies 20 are required for a ten-position selector micro-fluidic valve) which are symmetrically distributed about the cap member 31 in a manner applying a substantially uniform pressure gradient against proximal disk surface 43 of the stator device 38, which in turn biases the stator face 59 into abutting contact against the rotor face 54 of the rotor device 37. In turn, a uniform leak-tight seal is formed at the rotor/stator interface.

Simultaneously, the distal end of each elastomeric ferrule device 24 seals around the corresponding communication port 45 at the proximal disk surface 43 of the stator device 38 with a compression force that is a function of length or distance the elastomeric ferrule device is deflected when compressed between the support ring 30 and disk surface 43. Accordingly, the biasing spring force to some degree is dependent upon the elastomeric material, as well the total height compression thereof. As mentioned, the compression or clamping forces are applied by a minimum of two 4-40 UNC screws or bolts 53 passing through the slotted housing and secured into the actuator housing internally threaded holes. It will be appreciated, of course, that any conventional technique for mounting the cap member 31 to the housing 41 could be applied.

Figure 16:
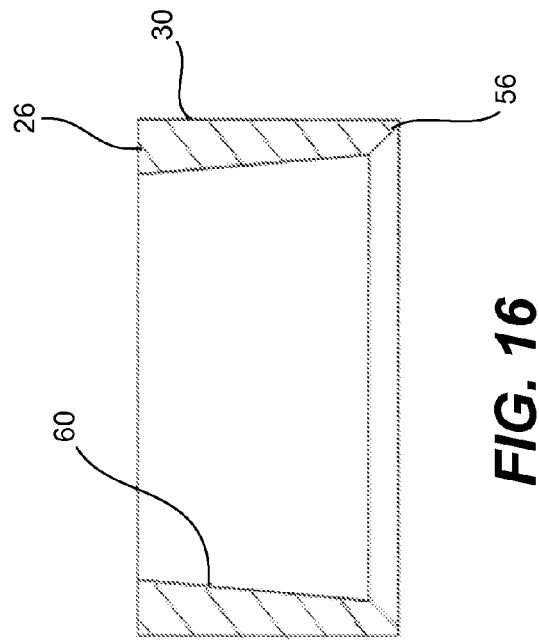
FIG. 16 is an enlarged, side elevation view, in cross-section, of a support ring for the tubing interface assembly of the present invention.

Referring now to the rigid support ring 30 of FIG. 16, this ring is preferably comprised of a metallic material such as stainless steel. It will be appreciated, of course, that other rigid materials can be utilized such as aluminum or high strength plastics.

Figure 5:
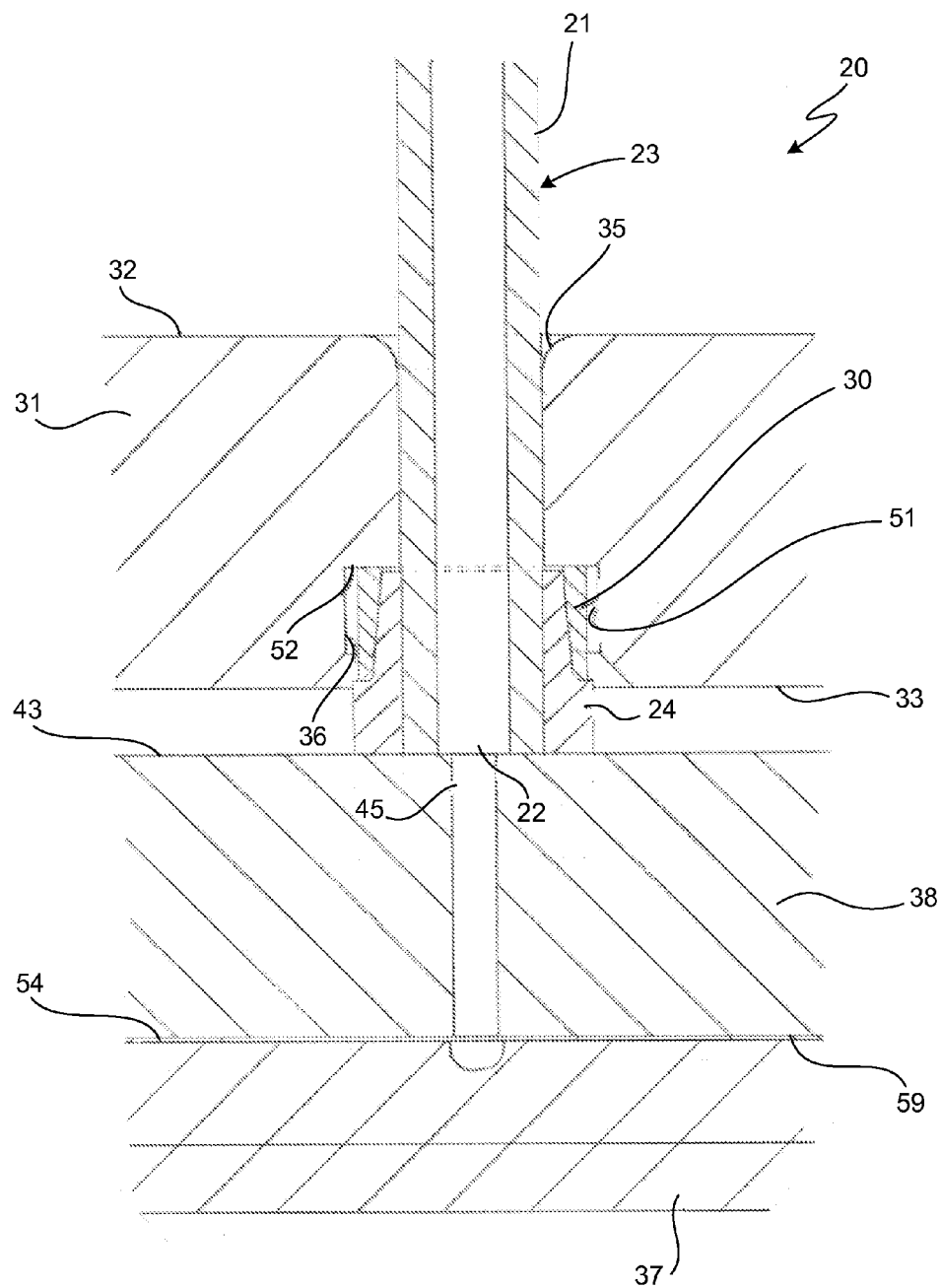
FIG. 5 is a fragmentary, enlarged, side elevation view, in cross-section, of the tubing interface assembly and the micro-fluidic valve assembly of FIG. 4.
Figure 6:
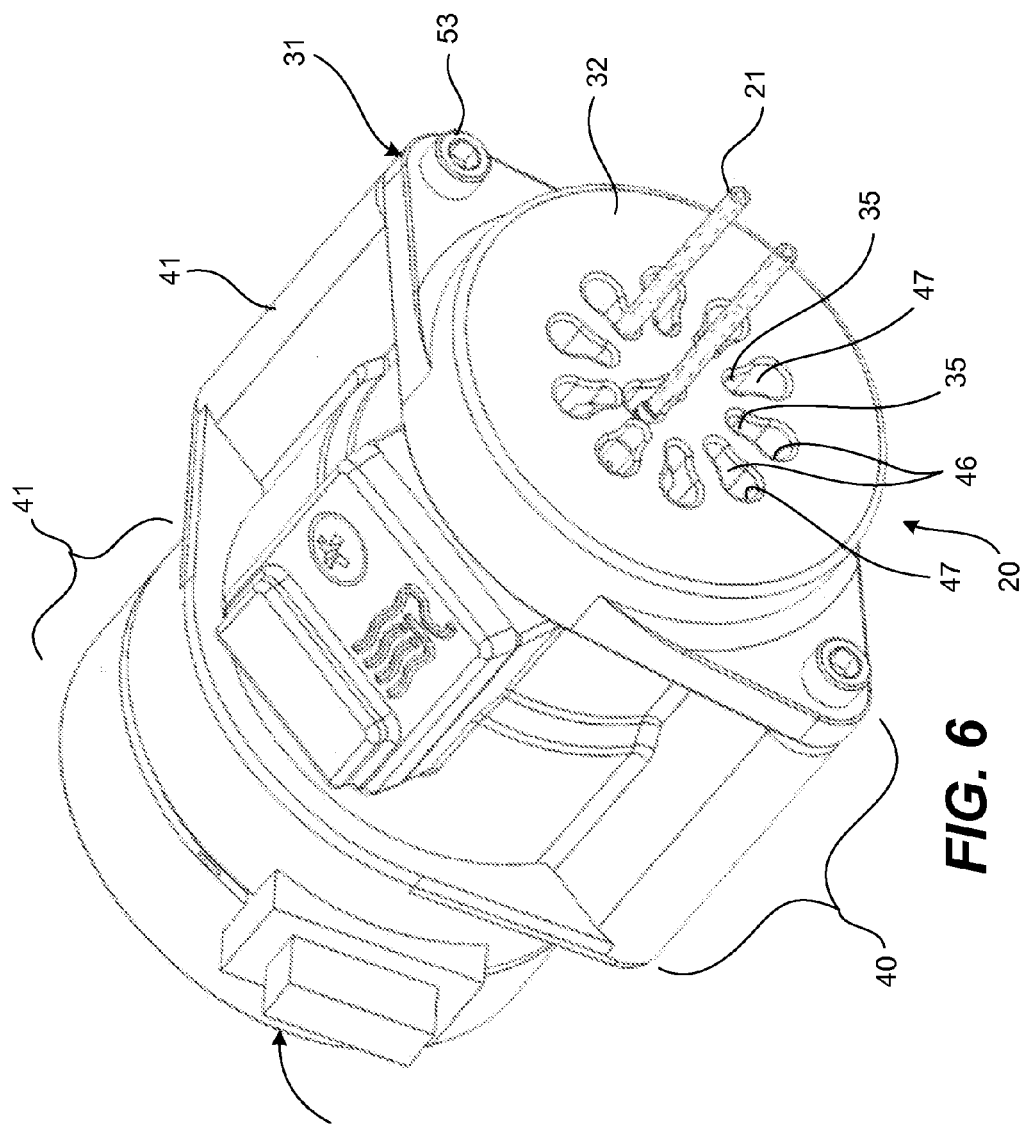
FIG. 6 is a top perspective view of an alternative tubing interface assembly and micro-fluidic valve assembly incorporating a slotted cap member.

Under compression, the support ring 30 axially transmits compressive forces from the cap member 31 to the elastomeric ferrule device 24. More particularly, as best shown in FIGS. 5 and 16, a proximal end 55 of the support ring 30 contacts a respective distally facing compression shoulder 52 of the cap member that partially defines each cup-shaped receiving recess 36. In turn, the compression forces are transmitted axially through the support ring 30 and on to the distal end 56 thereof which abuts a proximally facing ring contact shoulder 57 formed in each elastomeric ferrule device.

While one primary function of each rigid support ring 30 is to transmit the compressive forces from the cap member to the corresponding elastomeric ferrule device, another primary function is to provide a sufficient radial crimping force to the elastomeric ferrule device so that the axial position thereof along the corresponding tube member is maintained. Accordingly, during both mounting of the tubing interference assembly to the cap member, and during compression mounting of the cap member to the actuator assembly, the axial position of the respective ferrule device 40 is relatively sustained.

Accordingly, the support ring is configured to extend radially around a crimp portion 58 of the elastomeric ferrule device, providing a sufficient, albeit minute crimp force. To promote crimping, an interior crimp wall 60 of the support ring 30 is slightly tapered outwardly from the proximal end 55 to a slightly wider the distal end 56 thereof. FIG. 16 best illustrates the slope of the taper of the interior crimp wall 60 relative to longitudinal axis of the support ring 30.

The remaining distal compression portion 67 of the elastomeric ferrule device 24 provides the spring force when this portion is compressed between the distal end 56 of the support ring 30 and the proximal disk surface 43 of the stator device 38 when the cap member is mounted to the housing 41. To receivably accommodate both the elastomeric ferrule device 24 and the mounted support ring 30 in the respective cup-shaped receiving recess 36 of cap member 31, the outer diameter of the support ring is sized relatively similar to that of the outer diameter of the compression or distal portion 67 of the ferrule device. The outer diameter of the distal compression portion 67, as best viewed in FIGS. 13 and 15, is greater than that of the crimp portion 58. The diametric difference, of course, defines the ring-shaped contact shoulder 57.

Figure 17:
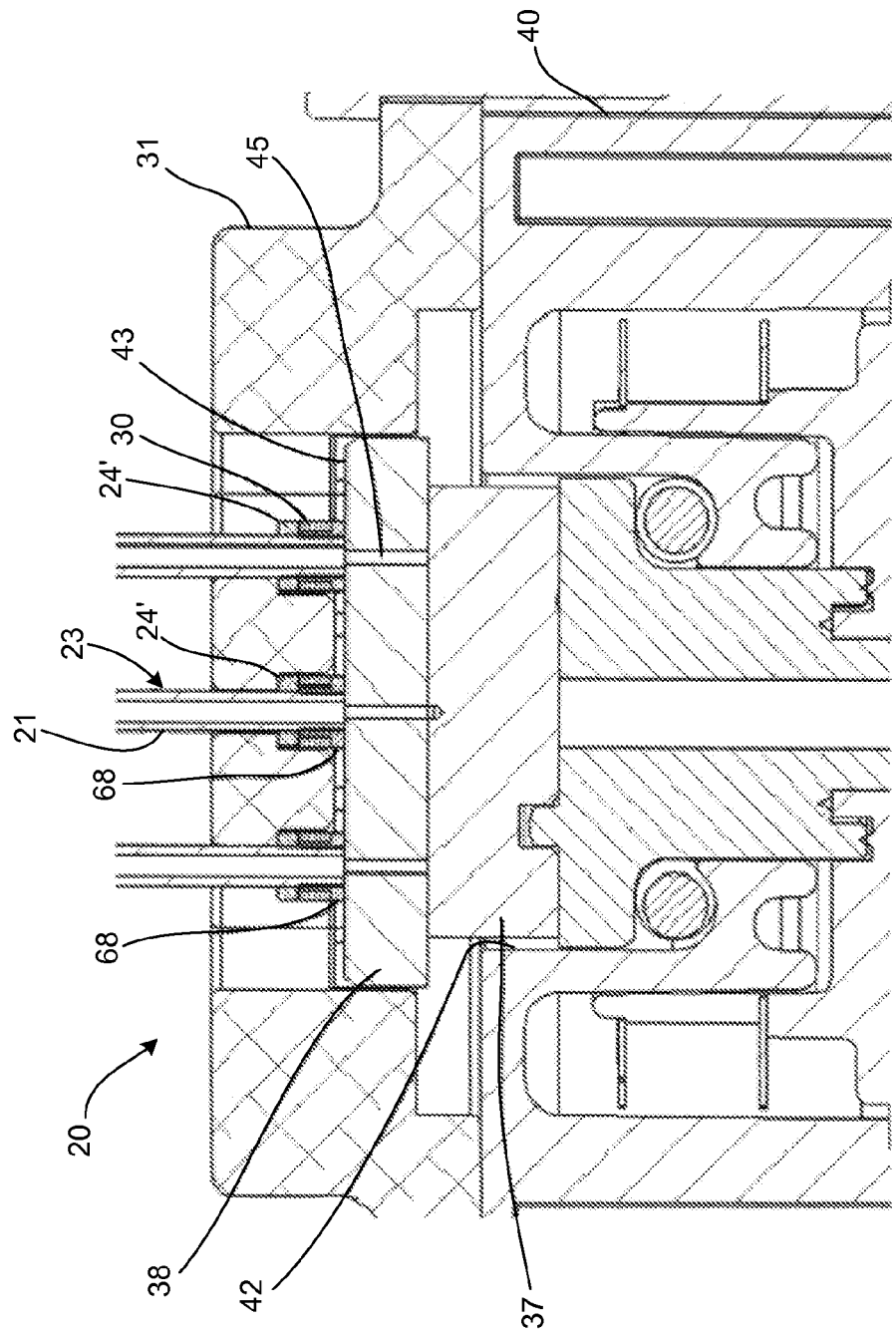
FIG. 17 is a fragmentary, enlarged, side elevation view, in cross-section, of an alternative embodiment tubing interface assembly.
Figure 18:
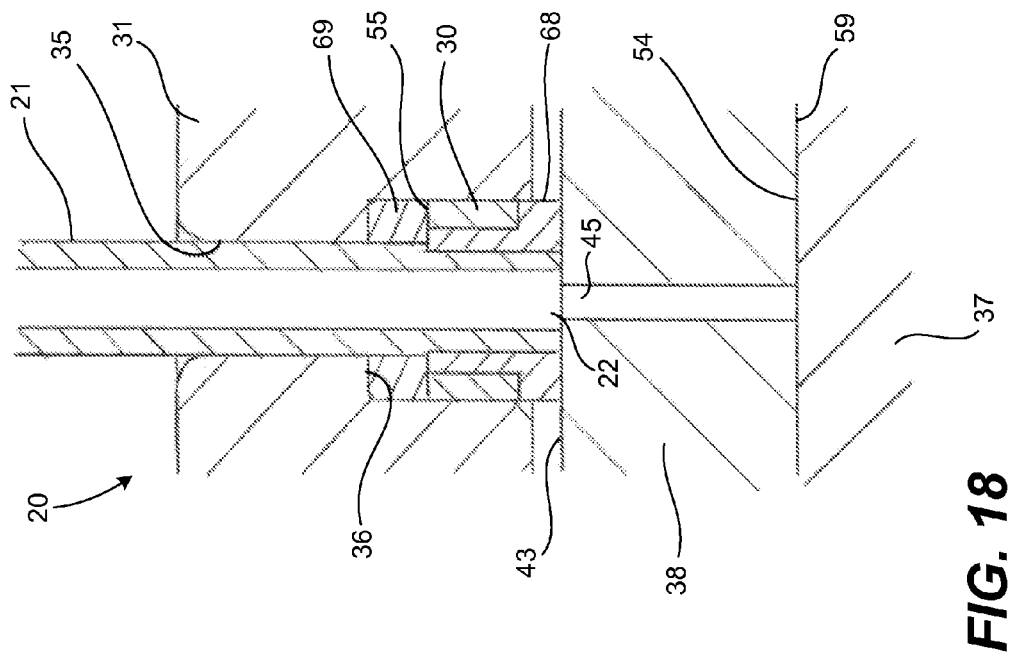
FIG. 18 is a fragmentary, enlarged, side elevation view, in cross-section, of the alternative embodiment tubing interface assembly and the micro-fluidic valve assembly of FIG. 17.

Referring now to FIGS. 17 and 18, an alternate embodiment is shown wherein the elastomeric ferrule device is supplanted with a ring or doughnut shaped elastomeric insert device 69 which is axially repositioned proximal to the rigid support ring 30. In this embodiment, the elastomeric insert device 69, which of course provides the sealing spring force, is compressed between the distally facing compression shoulder 52 of the receiving recess 36 and the proximal end 55 of the support ring 30. A conventional standard flat bottom PEEK ferrule device 68 is provided for sealing against the proximal disk surface 43 of the stator device. Hence, as mentioned, the ring-shaped elastomeric insert device 69, in this embodiment, applies a spring force biasing the flat bottom PEEK ferrule device 24' against the stator proximal disk surface 43, while in series collectively creating the sufficient compression force to seal the stator face 59 against the rotor face 54.

Figure 20:
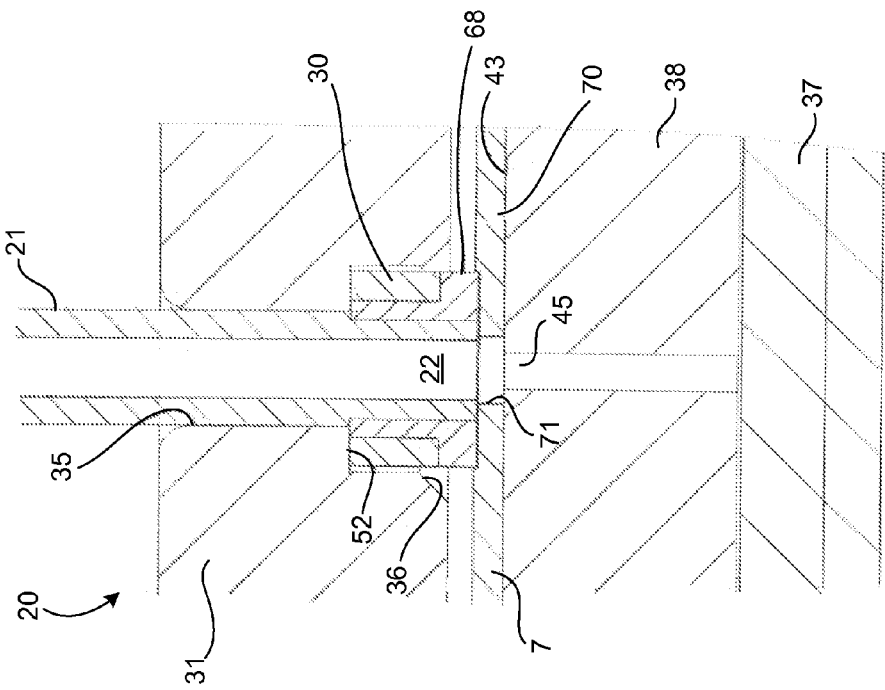
FIG. 20 is a fragmentary, enlarged, side elevation view, in cross-section, of the alternative embodiment tubing interface assembly and the micro-fluidic valve assembly of FIG. 19.
Figure 19:
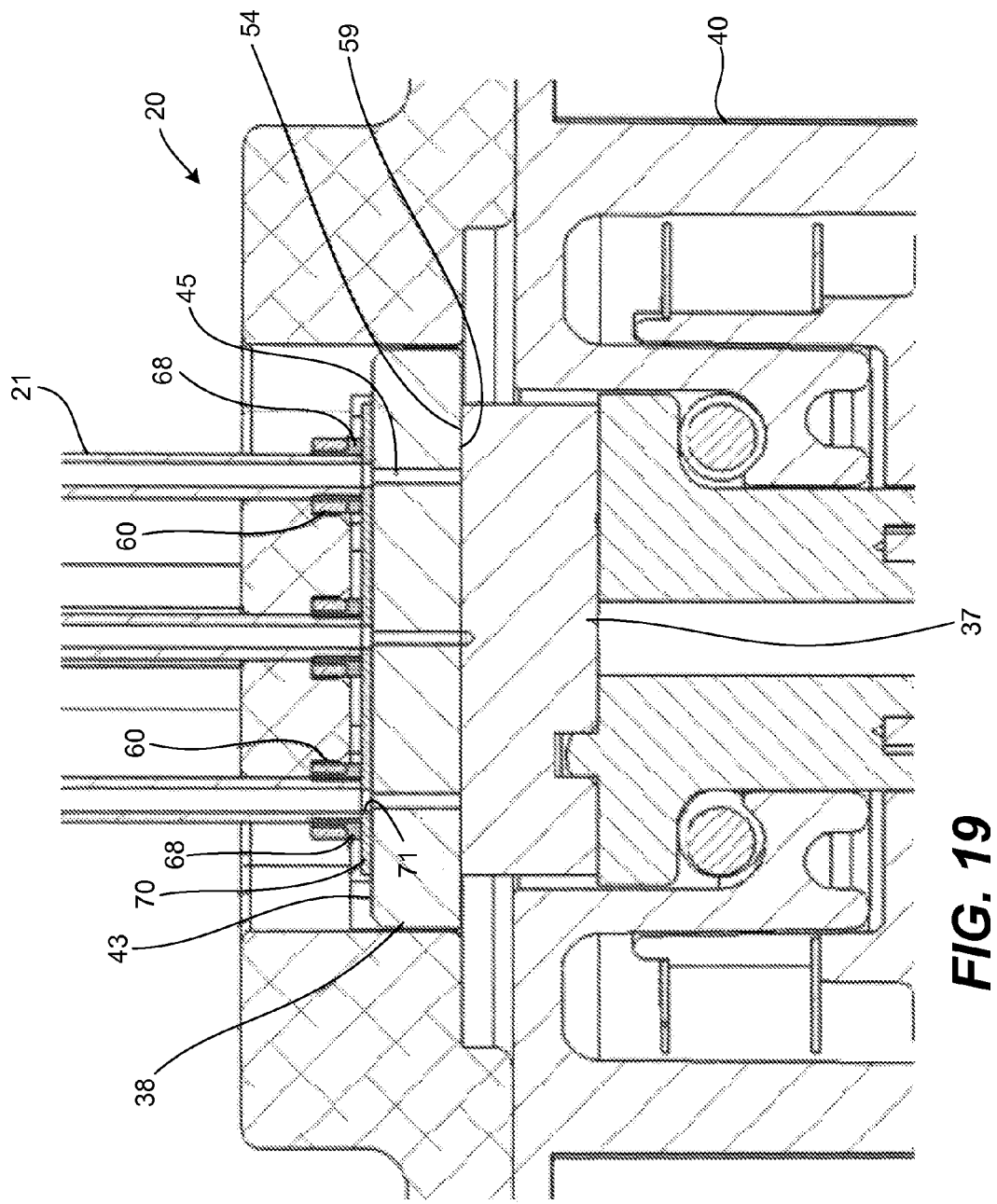
FIG. 19 is a fragmentary, enlarged, side elevation view, in cross-section, of another alternative embodiment tubing interface assembly.

In still another alternative configuration, as best viewed in FIGS. 19 and 20, a single piece elastomeric gasket 70 is disposed, and sandwiched, between a standard flat bottom PEEK ferrule device 68 and support ring 30, similar to the embodiment of FIGS. 17 and 18, and the proximal disk surface 43. The thin gasket 70 includes properly aligned apertures 71 which correspond to the pattern in fluid communication ports 45 defined by the stator device dist surface 43.

When the cap member 31 is mounted to the housing 41, the standard flat bottom PEEK ferrule device compresses the gasket, via support ring 30, against the disk surface 43. At the same time the elastomeric gasket 70 forms the fluid tight seal between the tube port 22 of the tube apparatus 23 and the corresponding fluid communication port 45 of the proximal disk surface 43, and further collectively generates the spring force necessary to seal the stator face 59 to the rotor face 54. The gasket material is similar to the elastomeric ferrule material and may be manufactured from santoprene, polyethylene or fluoroelastomer compounds.

Figure 21:
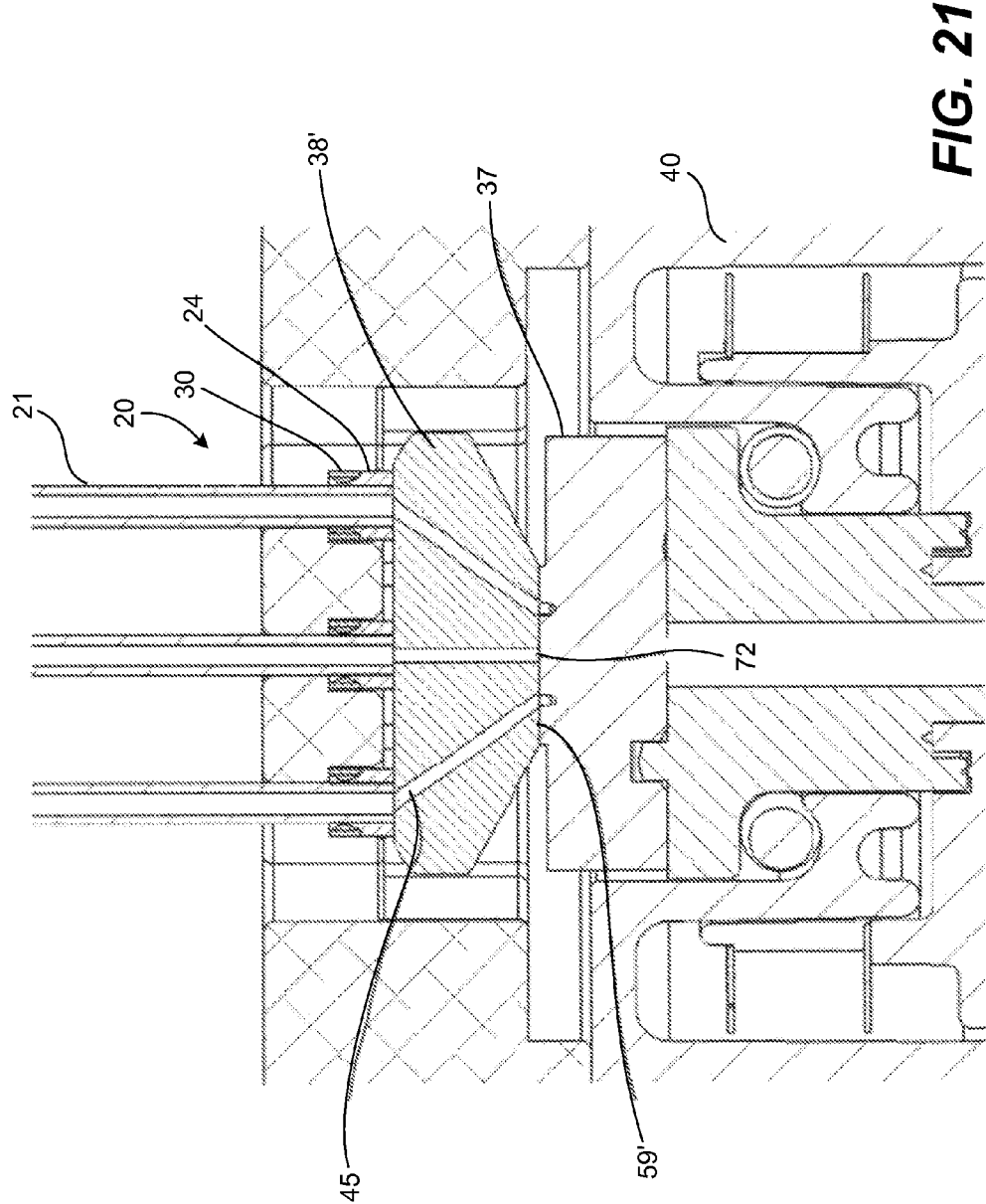
FIG. 21 is a fragmentary, enlarged, side elevation view, in cross-section, of still another alternative embodiment tubing interface assembly.

FIG. 21 illustrates yet another alternate embodiment which includes a conical-shaped stator device 38'. For valves requiring higher operating pressures, a conical-shaped stator device 38' incorporates angled, oval-shaped communication ports 72 at the stator face 59'. In this configuration, the bolt circle (approximately 0.460") is reduced from a larger diameter, where the elastomeric ferrule devices 23 seat, to a smaller diameter stator face 59' at the rotor/stator interface.

In this configuration, by reducing the bolt circle diameter of the conical-shaped stator device 38', the contact area of the rotor/stator interface for both the stator face 59' and the rotor face 54, is reduced. In turn, the compression force required to create a fluid-tight seal at a given pressure is decreased since the force is proportional to the contact area.

It will be appreciated that the present invention is not limited in size, and thus a variety of tubing OD and/or ID can be selected. Currently many variations of Peek tubing exist with different ID and a constant OD of $\frac{1}{16}^{th}$ for instance. The design of the elastomeric ferrule device can be adjusted in dimension to accommodate larger or even smaller OD tubing. The slotted cap member similarly can also be adjustably sized and dimensioned to accommodate differing sizes of the elastomeric ferrule and number of slots.

What is claimed is:

1. A tubing interface assembly for a micro-fluidic valve apparatus having a disk surface defining at least one fluid communication port, said tubing interface assembly comprising:

a tube apparatus including
        an elongated tube member having a tube port at a distal end thereof;
        an elastomeric ferrule device having a body member with a proximal end, a distal end, and a bore extending therethrough, said bore being formed and dimensioned for press-fit sliding receipt of the distal end of the tube member therethrough;

a rigid support ring device disposed around a portion of the ferrule body member in a press-fit manner; and a cap member having an exterior surface, an opposed interior surface, and a tube receiving passage extending from said exterior surface to said interior surface thereof, said tube receiving passage being formed and dimensioned for axial sliding receipt of a transverse cross sectional dimension of said tube member therethrough, said cap member further defining a cup-shaped receiving recess extending from said interior surface toward said exterior surface, said cup-shaped receiving recess being formed and dimensioned for axial receipt of at least said proximal end of the ferrule body member such that at least a distal portion of the body member extends distally past the interior surface of the cap member, said cap member defines a petal-shaped slot extending from said exterior surface to said interior surface, said petal-shaped slot having a ferrule passage on one side and tapering down to said tube receiving passage on an opposite end thereof, said ferrule passage being formed and dimensioned for sliding axial receipt of the ferrule device therethrough;

wherein when said cap member is mounted to said valve apparatus in a manner aligning said tube port with said fluid communication port of the disk surface, said elastomeric ferrule device compressively cooperates with the cap member to form a fluid-tight seal between said tube port and said fluid communication port.

2. The tubing interface assembly according to claim 1, wherein
said body member of said elastomeric ferrule device has a modulus of elasticity in the range of about 500 psi to about 20,000 psi.

3. The tubing interface assembly according to claim 1, wherein
said cup-shaped receiving recess is partially defined by a distally facing contact shoulder formed to compressively seat and contact at least one of the ferrule body member and the support ring thereagainst.

4. The tubing interface assembly according to claim 3, wherein
the ferrule body member includes a compression portion having a first diameter, and a crimp portion having a second diameter, said second diameter being less than the first diameter such that a ring contact shoulder is formed therebetween, said crimp portion is formed for sliding receipt of said support ring such that a distal edge thereof abuts against said ring contact shoulder for compressive deformation of the ferrule compression portion when said cap member is mounted to the valve apparatus.

5. The tubing interface assembly according to claim 4, wherein
a proximal end portion of said support ring seats against said contact shoulder of said cap member.

6. A tubing interface assembly for a micro-fluidic valve apparatus having a disk surface having a plurality of fluid communication ports radially spaced about an axis thereof, said tubing interface assembly comprising:
a plurality of tubing assemblies each including
an elongated tube member having a tube port at a distal end thereof;
an elastomeric ferrule device having a body member with a proximal end, a distal end, and a bore extending therethrough, said bore being formed and dimensioned for sliding receipt of the distal end of the tube member therethrough; and a rigid support ring device disposed around a portion of the respective ferrule body member; and a rigid cap member having an exterior surface, an opposed interior surface, and a plurality of tube receiving passage extending from said exterior surface to said interior surface thereof and spaced thereabout in a manner such that each tube receiving passage is aligned with a respective one of the plurality of fluid communication ports, each said tube receiving passage being formed and dimensioned for axial sliding receipt of a respective tube member therethrough, said cap member further defining a plurality of ferrule receiving recesses each corresponding to a respective tube receiving passage and extending proximally from said interior surface, each ferrule receiving recess being formed and dimensioned for axial receipt of at least said proximal end of the ferrule body member and said support ring, said cap member defines a plurality of petal-shaped slots extending from said exterior surface to said interior surface, and each corresponding to a respective tube receiving passage, each petal-shaped slot having a ferrule passage on one side and tapering down to said tube receiving passage on an opposite end thereof, said ferrule passage being is formed and dimensioned for sliding axial receipt of a respective ferrule device therethrough;

wherein when said cap member is mounted to said valve apparatus, each respective support ring and each respective elastomeric ferrule device compressively cooperate with the cap member to form a fluid-tight seal between each respective tube port and each respective fluid communication port.

7. The tubing interface assembly according to claim 6, wherein
each said ferrule receiving recess is cup-shaped, and is partially defined by a distally facing contact shoulder formed to compressively seat and contact at least one of the ferrule body member and the support ring thereagainst.

8. The tubing interface assembly according to claim 7, wherein
each ferrule body member includes a compression portion having a first diameter, and a crimp portion having a second diameter, said second diameter being less than the first diameter such that a ring contact shoulder is formed therebetween, said crimp portion is formed for sliding receipt of a respective support ring such that a distal edge thereof abuts against a respective ring contact shoulder for compressive deformation of the respective ferrule compression portion when said cap member is mounted to the valve apparatus.

9. The tubing interface assembly according to claim 8, wherein
a proximal end portion of each respective support ring seats against a respective contact shoulder of said cap member.

10. A micro-fluidic valve apparatus comprising:
a housing having a proximal opening;
a fluid distribution unit disposed in said proximal opening, and having a proximal contact surface defining two or more fluid communication ports; and
a tubing interface assembly comprising:
two or more tubing assemblies each including
an elongated tube member having a tube port at a distal end thereof;

an elastomeric ferrule device having a body member with a proximal end, a distal end, and a bore extending therethrough, said bore being formed and dimensioned for press-fit sliding receipt of the distal end of the respective tube member therethrough; and a rigid support ring device disposed around a portion of the respective ferrule body member; and a cap member having an exterior surface, an opposed interior surface, and two or more tube receiving passages each extending from said exterior surface to said interior surface thereof, each said tube receiving passage being formed and dimensioned for axial sliding receipt of a transverse cross sectional dimension of a respective tube member therethrough, said cap member further defining two or more cup-shaped receiving recesses each extending from said interior surface toward said exterior surface, and each corresponding to a respective tube receiving passage, each said cup-shaped receiving recess being formed and dimensioned for axial receipt of at least said a respective proximal end of the ferrule body member and said support ring such that at least a respective distal portion of the body member extends distally past the interior surface of the cap member, said cap member defines two or more petal-shaped slots extending from said exterior surface to said interior surface, each petal-shaped slot corresponding to a respective tube receiving passage, and each having a ferrule passage on one side and tapering down to said tube receiving passage on an opposite end thereof, each said ferrule passage being is formed and dimensioned for sliding axial receipt of a respective ferrule device therethrough;

wherein when said cap member is mounted to said housing in a manner aligning a respective tube port with a respective fluid communication port of the disk surface, each respective support ring and each respective said elastomeric ferrule device compressively cooperate with the cap member to form a fluid-tight seal between the corresponding tube port and the corresponding fluid communication port.

11. The micro-fluidic valve apparatus according to claim 10, wherein an inner diameter of each respective support ring is defined by an interior wall tapering outwardly from the proximal end to the distal end thereof.

12. The micro-fluidic valve apparatus according to claim 10, wherein each said cup-shaped receiving recess is partially defined by a distally facing contact shoulder formed to compressively seat and contact a respective ferrule body member and a respective support ring thereagainst.

13. The micro-fluidic valve apparatus according to claim 12, wherein each ferrule body member includes a compression portion having a first diameter, and a crimp portion having a second diameter, said second diameter being less than the first diameter such that a ring contact shoulder is formed therebetween, said crimp portion is formed for sliding receipt of a respective support ring such that a respective distal edge thereof abuts against a respective ring contact shoulder for compressive deformation of the corresponding ferrule compression portion when said cap member is mounted to the valve apparatus.

14. The micro-fluidic valve apparatus according to claim 13, wherein a proximal end portion of each support ring seats against a respective contact shoulder of corresponding petal-shaped slot.

15. The micro-fluidic valve apparatus according to claim 14, wherein each said body member of said elastomeric ferrule device has a modulus of elasticity in the range of about 500 psi to about 20,000 psi.

\* \* \* \* \*